United States Patent
Kita et al.

(10) Patent No.: US 11,123,528 B2
(45) Date of Patent: Sep. 21, 2021

(54) BALLOON CATHETER AND METHOD FOR MANUFACTURING SAME

(71) Applicant: KANEKA CORPORATION, Osaka (JP)

(72) Inventors: Soichiro Kita, Osaka (JP); Masao Sato, Osaka (JP); Hitoshi Tahara, Osaka (JP); Ryoji Nakano, Osaka (JP); Motokazu Watanabe, Osaka (JP); Takuji Nishide, Osaka (JP)

(73) Assignee: KANEKA CORPORATION, Osaka (JP)

( * ) Notice: Subject to any disclaimer, the term of this patent is extended or adjusted under 35 U.S.C. 154(b) by 180 days.

(21) Appl. No.: 16/240,131

(22) Filed: Jan. 4, 2019

(65) Prior Publication Data

US 2019/0134359 A1 May 9, 2019

Related U.S. Application Data

(63) Continuation of application No. PCT/JP2017/023964, filed on Jun. 29, 2017.

(30) Foreign Application Priority Data

Jul. 4, 2016 (JP) .............................. JP2016-132850

(51) Int. Cl.
*A61M 25/10* (2013.01)
*A61L 29/14* (2006.01)
(Continued)

(52) U.S. Cl.
CPC ........... *A61M 25/104* (2013.01); *A61L 29/14* (2013.01); *A61M 25/00* (2013.01); *A61M 25/10* (2013.01);
(Continued)

(58) Field of Classification Search
CPC .... A61M 25/104; A61M 25/10; A61M 25/00; A61M 25/1002; A61M 25/1029;
(Continued)

(56) References Cited

U.S. PATENT DOCUMENTS 5,102,402 A 4/1992 Dror et al.
5,304,121 A 4/1994 Sahatjian
(Continued)

FOREIGN PATENT DOCUMENTS

JP H05505132 A 8/1993
JP 2008529740 A 8/2008
(Continued)

OTHER PUBLICATIONS

International Search Report issued in International Application No. PCT/JP2017/023964; dated Sep. 12, 2017 (2 pages).
(Continued)

*Primary Examiner* — Theodore J Stigell
*Assistant Examiner* — Rachel T. Smith
(74) *Attorney, Agent, or Firm* — Osha Bergman Watanabe & Burton LLP

(57) ABSTRACT

A balloon catheter includes a shaft and a balloon having one or more fold lines. The balloon is disposed outside the shaft, and the balloon includes one or more first regions and one or more second regions. The first region retains medicine on an outer surface of the balloon. The second region retains less medicine than the first region or retains no medicine.

6 Claims, 8 Drawing Sheets

(51) Int. Cl.
*A61M 25/00* (2006.01)
*A61L 29/08* (2006.01)
*B29L 31/00* (2006.01)

(52) U.S. Cl.
CPC .... *A61M 25/1002* (2013.01); *A61M 25/1029* (2013.01); *A61L 29/085* (2013.01); *A61M 25/1038* (2013.01); *A61M 2025/1004* (2013.01); *A61M 2025/105* (2013.01); *A61M 2025/1031* (2013.01); *A61M 2025/1075* (2013.01); *A61M 2025/1088* (2013.01); *B29L 2031/7543* (2013.01)

(58) Field of Classification Search
CPC ...... A61M 25/1038; A61M 2025/1004; A61M 2025/1031; A61M 2025/105; A61M 2025/1075; A61M 2025/1088; A61L 29/14; A61L 29/085; B29L 2031/7543
See application file for complete search history.

(56) References Cited

U.S. PATENT DOCUMENTS

| | | | |
|---|---|---|---|
| 5,324,261 | A | 6/1994 | Amundson et al. |
| 5,370,614 | A | 12/1994 | Amundson et al. |
| 5,893,840 | A | 4/1999 | Hull et al. |
| 2006/0020243 | A1 | 1/2006 | Speck et al. |
| 2006/0182873 | A1 | 8/2006 | Klisch et al. |
| 2009/0054837 | A1 | 2/2009 | Von Holst et al. |
| 2009/0226502 | A1 | 9/2009 | Chen |
| 2009/0227948 | A1 | 9/2009 | Chen et al. |
| 2009/0227949 | A1 | 9/2009 | Knapp et al. |
| 2010/0228228 | A1 | 9/2010 | Speck et al. |
| 2011/0270226 | A1 | 11/2011 | Kocur et al. |
| 2011/0301697 | A1 | 12/2011 | Hoffmann et al. |
| 2012/0053517 | A1 | 3/2012 | Chen et al. |
| 2012/0150142 | A1 | 6/2012 | Weber et al. |
| 2012/0232640 | A1 | 9/2012 | Horvers |
| 2012/0253380 | A1* | 10/2012 | Venturelli ........... A61M 25/104 606/194 |
| 2013/0066268 | A1 | 3/2013 | Von Holst et al. |
| 2013/0231638 | A1 | 9/2013 | Speck et al. |
| 2013/0303982 | A1 | 11/2013 | Morero et al. |
| 2013/0303983 | A1* | 11/2013 | Barbick .................. A61P 35/00 604/103.02 |
| 2014/0228750 | A1 | 8/2014 | Speck et al. |
| 2014/0228751 | A1 | 8/2014 | Speck et al. |
| 2014/0228752 | A1 | 8/2014 | Speck et al. |
| 2014/0378896 | A1 | 12/2014 | Venturelli |
| 2015/0024116 | A1 | 1/2015 | Matson et al. |
| 2016/0121027 | A1* | 5/2016 | Mani ...................... A61L 31/10 604/509 |
| 2016/0158507 | A1 | 6/2016 | Speck et al. |

FOREIGN PATENT DOCUMENTS

| | | |
|---|---|---|
| JP | 2010214205 A | 9/2010 |
| JP | 2011504130 A | 2/2011 |
| JP | 2011513004 A | 4/2011 |
| JP | 2012166038 A | 9/2012 |
| JP | 2013099432 A | 5/2013 |
| JP | 2014155657 A | 8/2014 |
| JP | 2015217260 A | 12/2015 |
| WO | 2009111712 A1 | 9/2009 |
| WO | 2012166819 A1 | 12/2012 |

OTHER PUBLICATIONS

Written Opinion of the International Searching Authority issued in International Application No. PCT/JP2017/023964; dated Sep. 12, 2017 (5 pages).

Supplementary Partial European Search Report issued in corresponding European Application No. 17824123; dated Feb. 5, 2020 (5 pages).

\* cited by examiner

[Fig. 1]
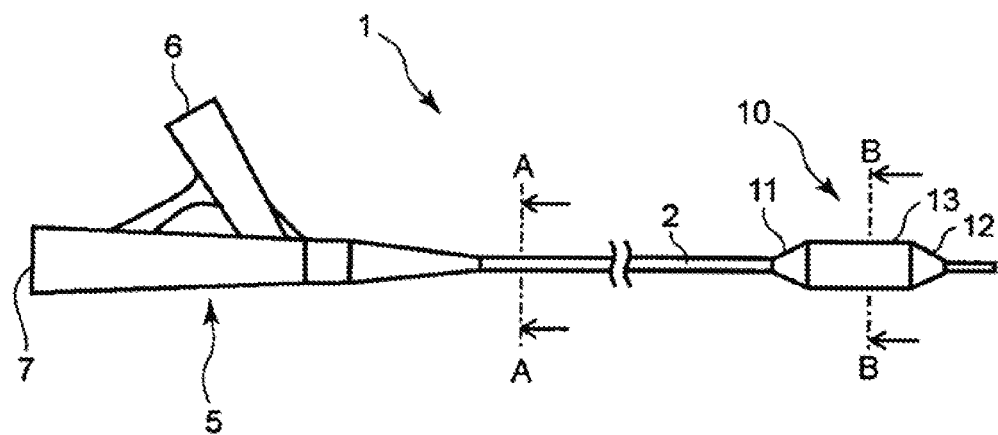
[Fig. 2A]
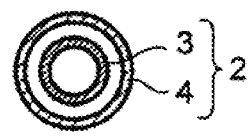
[Fig. 2B]
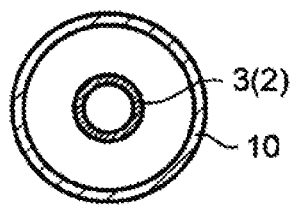

[Fig. 3]
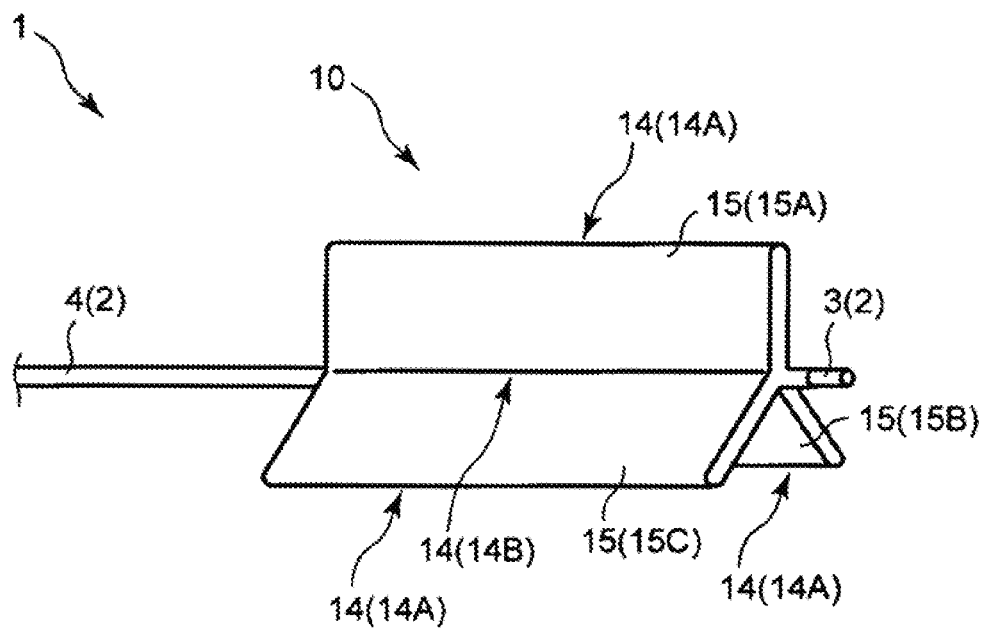
[Fig. 4]
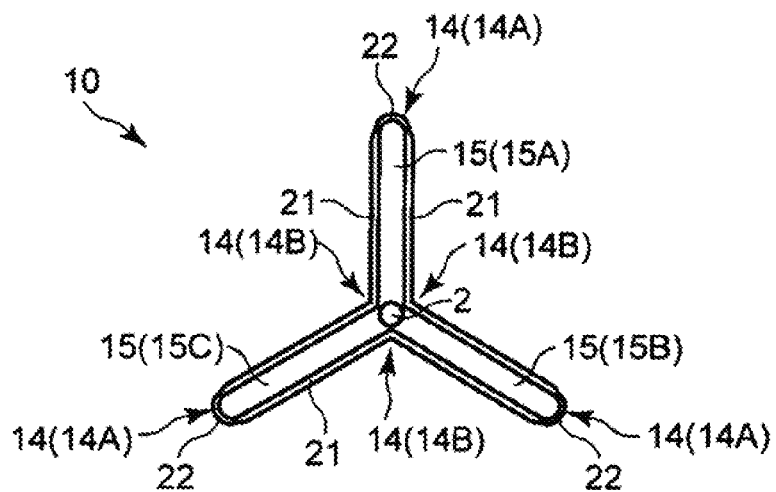

[Fig. 5]
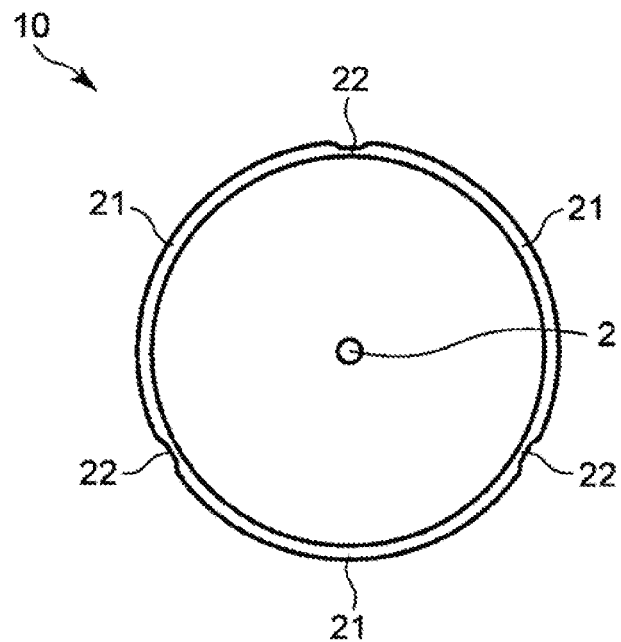
[Fig. 6]
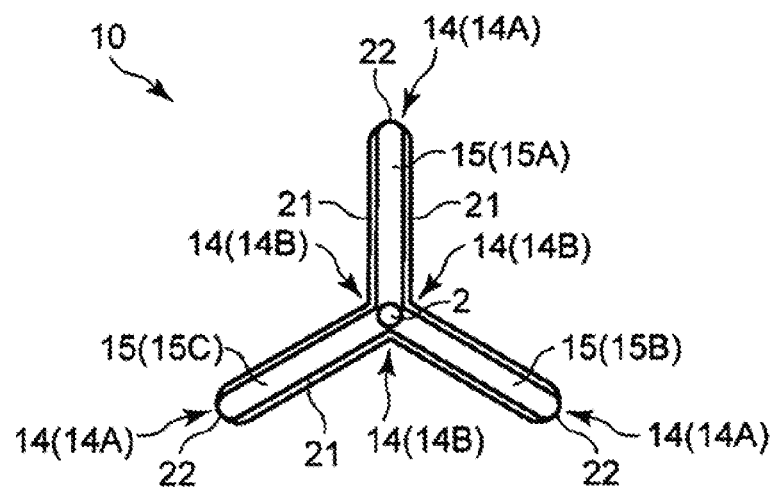

[Fig. 7]
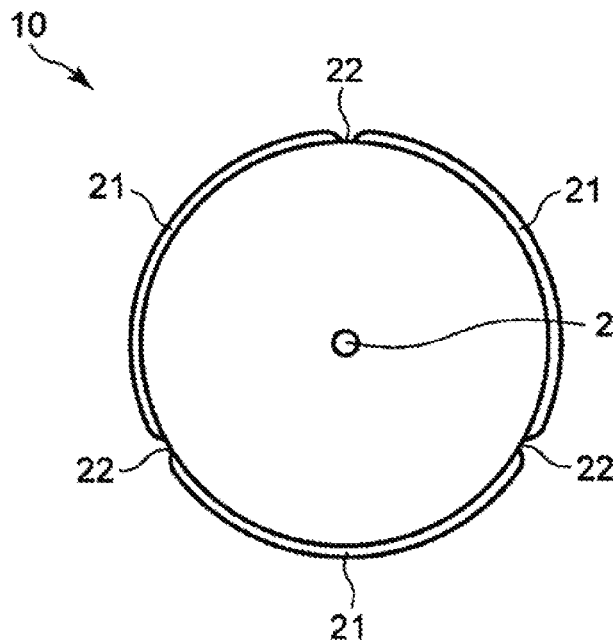
[Fig. 8]
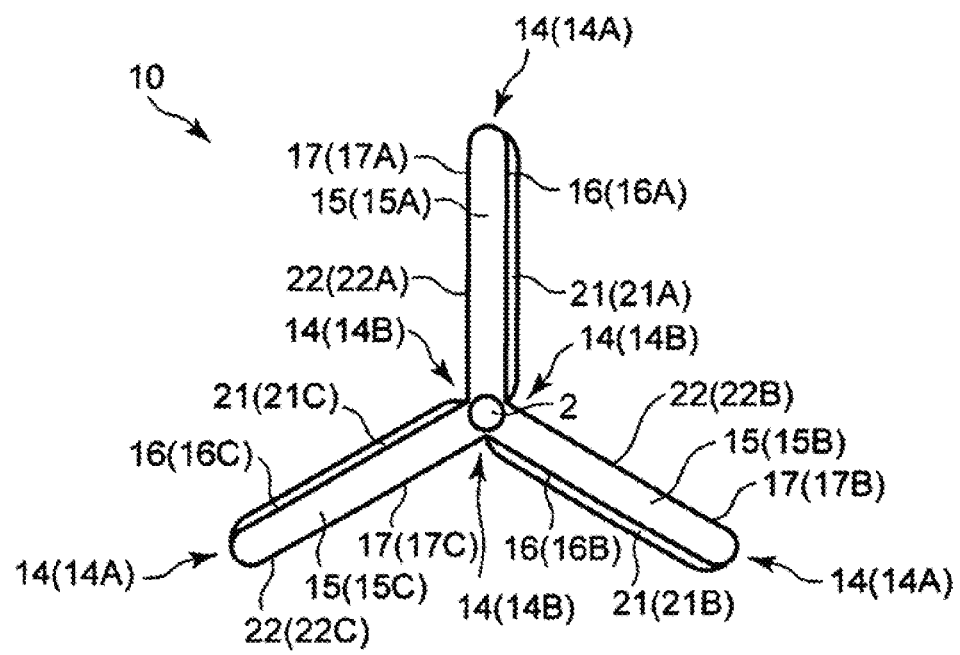

[Fig. 9]
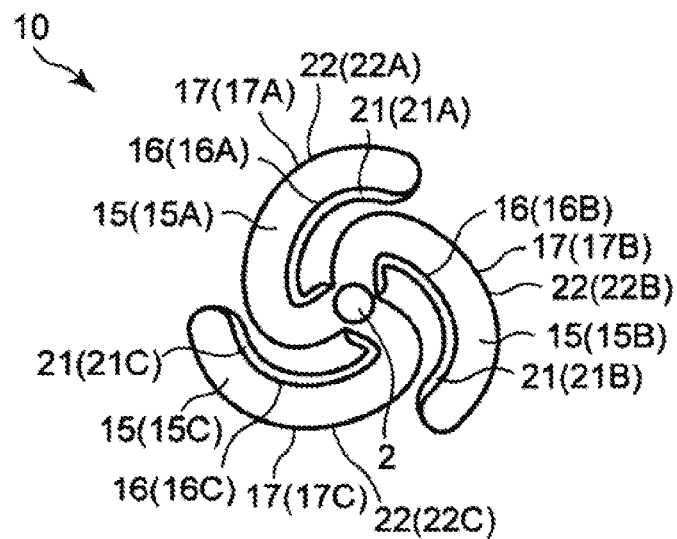
[Fig. 10]
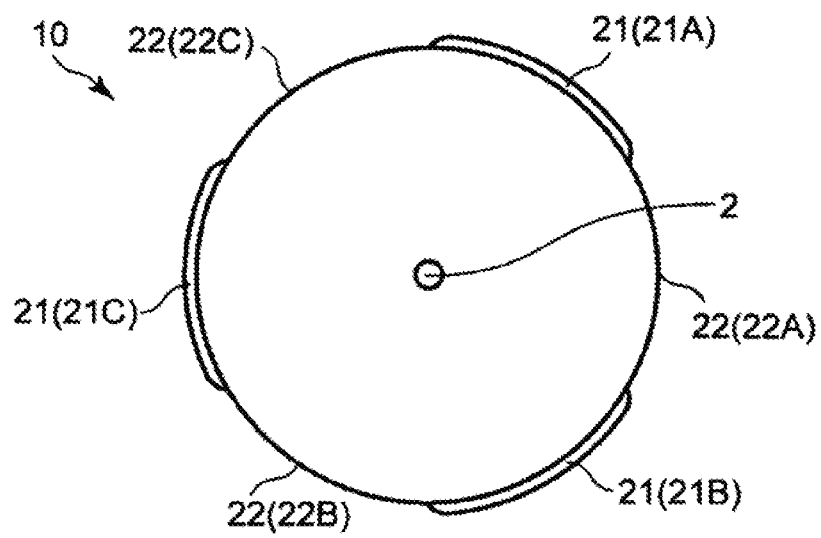

[Fig. 11]
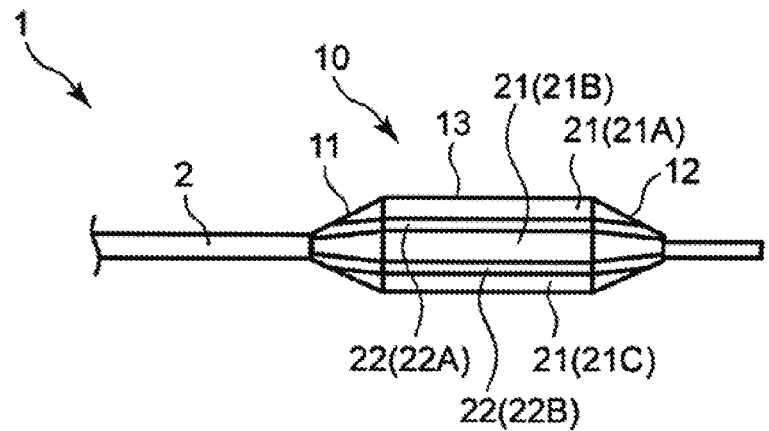
[Fig. 12]
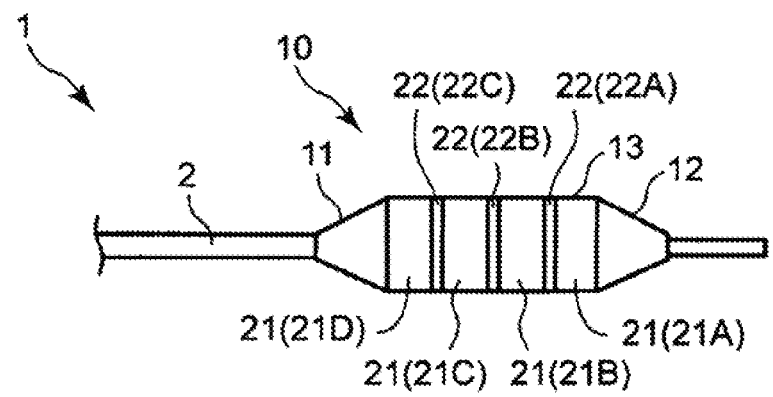
[Fig. 13]
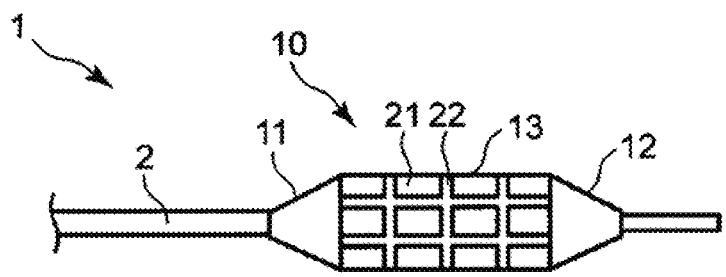

[Fig. 14]
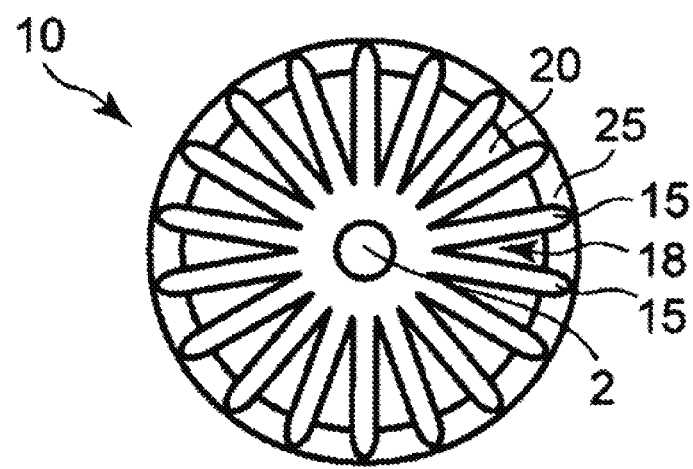
[Fig. 15]
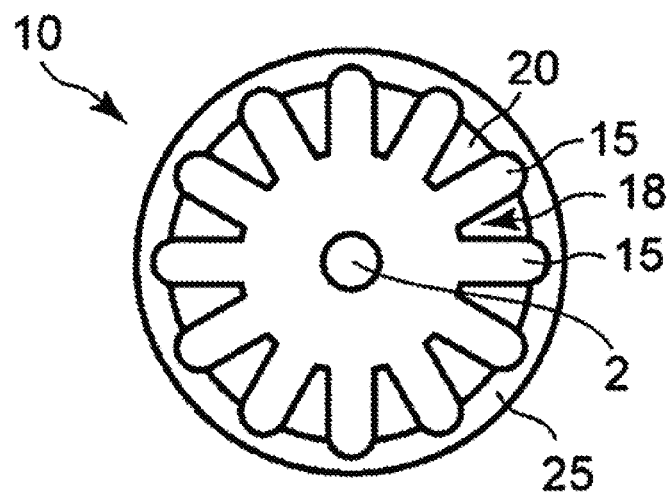

[Fig. 16]
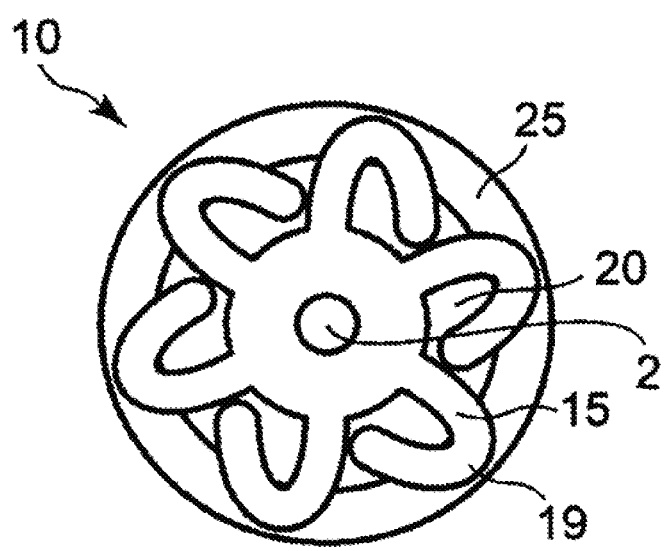

BALLOON CATHETER AND METHOD FOR MANUFACTURING SAME

TECHNICAL FIELD

One or more embodiments of the present invention relate to a balloon catheter that prevents medicine from eluting and a method for manufacturing the same.

BACKGROUND

It has been known that various diseases are caused by stagnation of blood circulation due to narrowed blood vessels, which are channels through which blood circulates in the body. In particular, narrowed coronary arteries supplying blood to the heart may cause serious diseases such as angina pectoris and myocardial infarction. As one of methods for treating such a narrowed portion of blood vessels, angioplasty (for example, PTA, PTCA) has been used for dilating the narrowed portion using a balloon catheter. Angioplasty is widely performed because it is a minimally invasive therapy that does not require thoracotomy such as bypass surgery.

Meanwhile, the angioplasty sometimes causes the narrowed portion that has been dilated to develop restenosis. As one of treatment methods for reducing frequency of the restenosis (restenosis rate), a treatment employing a drug-eluting stent having a medicine layer on its surface has been used. A drug-eluting balloon catheter retaining medicine on its balloon has also been proposed (for example, Patent Documents 1 to 4). With the drug-eluting balloon catheter, medicine can be transferred to a vascular wall by inflating the balloon at a lesion site, and this is expected to prevent the occurrence of restenosis. Advantages of the treatment method using the drug-eluting balloon catheter include that no foreign substance is left in the body and that a small blood vessel into which a stent cannot be inserted can also be a target for the treatment.

To make it easier for a balloon catheter to pass during being delivered, there has been proposed a configuration in which a deflated balloon is folded with wings of the balloon being wrapped around a shaft of a catheter to reduce the outer diameter of the balloon (for example, Patent Documents 5 and 6) and a configuration in which a material having high expandability is employed for a balloon so as to reduce the outer diameter of the deflated balloon (for example, Patent Document 7). With such configurations, it is possible to prevent medicine retained on the balloon portion from peeling or eluting due to contact of the medicine with blood at a site other than a lesion site while the medicine is being delivered to a narrowed portion or the lesion site (hereinafter, referred to as "while being delivered).

PATENT DOCUMENTS

Patent Document 1: U.S. Pat. No. 5,304,121
Patent Document 2: JP-A-H05-505132
Patent Document 3: JP-A-2008-529740
Patent Document 4: JP-A-2015-217260
Patent Document 5: JP-A-2010-214205
Patent Document 6: JP-A-2014-155657
Patent Document 7: JP-A-2013-99432

SUMMARY

However, when a balloon that has been inflated and coated with medicine on its outer surface is deflated and folded, the medicine layer having a higher hardness than the balloon can hardly respond to the flexibility of the balloon, so that the medicine layer located on a fold line may have rifts or cracks (hereinafter, referred to as "cracks"), which may cause fall of the medicine layer or elution of the medicine.

Generally a balloon is entirely uniformly coated with medicine because of a demand to apply as much medicine as possible to the balloon in order to secure the medicine needed for treatment of a narrowed portion or a lesion site. However, when the medicine is uniformly applied to the entire balloon, one crack may trigger spread of cracks over the entire balloon, and the drug may fall everywhere in the balloon. For example, if the medicine falls at an unintended area (for example, an area other than a target vascular lesion) when the balloon catheter is used for treatment, serious side effects may occur, and it is extremely important to prevent such fall of the medicine during the treatment. Meanwhile, to obtain sufficient therapeutic effects, it is necessary to make most of the medicine coating the balloon reach a target lesion without any loss while being delivered.

Furthermore, cracks also occur in processes other than treatment with a balloon, such as a process for manufacturing the balloon or preparing the treatment, and such cracks may cause loss of medicine.

One or more embodiments of the present invention provide a balloon catheter capable of preventing medicine from unintentionally eluting into blood while being delivered and from falling at a portion other than a target lesion, and a method for manufacturing the balloon catheter.

A first balloon catheter according to one or more embodiments of the present invention comprising:
a shaft, and
a balloon disposed outside the shaft and having a fold line, wherein the balloon comprises a first region that retains medicine on an outer surface and a second region that retains less medicine than the first region or that retains no medicine.

It may be preferable that the second region retains no medicine in the first balloon catheter.

The first balloon catheter may be preferable, wherein the first region is divided into at least two or more segments.

The first balloon catheter may be preferable, wherein the second region is disposed at the fold line.

The first balloon catheter may be preferable, wherein the first region and the second region are alternately disposed in a circumferential direction of the balloon.

The first balloon catheter may be preferable, wherein the balloon comprises a plurality of wings each having one main surface ("first surface") and other main surface ("second surface") in a deflated state, the first region is disposed on the one main surface of each of the plurality of wings, and the one main surface of each of the plurality of wings are disposed inwardly more than the other main surface in a radial direction of the balloon in a state in which the balloon is folded.

The first balloon catheter may be preferable, wherein the amount of medicine retained at an edge part of the first region of the balloon gradually decreases toward the second region.

A second balloon catheter according to one or more embodiments of the present invention comprising:
a shaft, and a balloon disposed outside the shaft and retaining medicine on an outer surface, wherein the balloon has 7 or more and 20 or less wings in a deflated state.

The second balloon catheter may be preferable, wherein the medicine is an antiproliferative agent or an immunosuppressive agent.

A first method for manufacturing a balloon catheter according to one or more embodiments of the present invention comprises: preparing a balloon having a plurality of wings in a deflated state, inflating the balloon and forming a mask in a predetermined region of the balloon, attaching medicine to the balloon on which the mask has been formed, removing the mask, and deflating the balloon from which the mask has been removed and folding the wings of the balloon.

A second method for manufacturing a balloon catheter according to one or more embodiments of the present invention comprises: preparing a balloon having a plurality of wings in a deflated state, inflating the balloon and applying medicine to a predetermined region of the balloon, and deflating the balloon to which the medicine has been applied and folding the wings of the balloon.

A third method for manufacturing a balloon catheter according to one or more embodiments of the present invention comprises: preparing a balloon having a plurality of wings in a deflated state, inflating the balloon and attaching medicine to the balloon, removing the medicine in a predetermined region, and deflating the balloon from which the medicine has been removed and folding the wings of the balloon.

A fourth method for manufacturing a balloon catheter according to one or more embodiments of the present invention comprises: preparing a balloon having a plurality of wings in a deflated state, folding the wings of the balloon in the deflated state, and attaching medicine to the folded balloon.

A fifth method for manufacturing a balloon catheter according to one or more embodiments of the present invention comprises: preparing a balloon having a plurality of wings in a deflated state, forming a mask in a predetermined region of the balloon in the deflated state, attaching medicine to the balloon on which the mask has been formed, removing the mask, and folding the wings of the balloon.

A sixth method for manufacturing a balloon catheter according to one or more embodiments of the present invention comprises: preparing a balloon having a plurality of wings in a deflated state, applying medicine to a predetermined region of the balloon in the deflated state, and folding the wings of the balloon.

A seventh method for manufacturing a balloon catheter according to one or more embodiments of the present invention comprises: preparing a balloon having a plurality of wings in a deflated state, attaching medicine the balloon in the deflated state, removing the medicine in a predetermined region, and folding the wings of the balloon from which the medicine has been removed.

The first to the seventh methods for manufacturing a balloon catheter according to one or more embodiments of the present invention further comprising: forming a coating layer on the balloon in the deflated state with the wings being folded.

A first balloon catheter according to one or more embodiments of the present invention has a first region and a second region. In cases where the amount of medicine retained in the second region is less than the amount of medicine retained in the first region, fall or elution of the medicine can be prevented that is caused by spread of cracks generated in the first region retaining the medicine over the entire balloon. In addition, in cases where no medicine is retained in the second region, cracks generated in the first region remain within the first region, and thus, do not spread to an adjacent first region and do not spread over the entire balloon.

A balloon of a second balloon catheter according to one or more embodiments of the present invention has 7 or more and 20 or less wings in a deflated state, whereby the balloon easily retains medicine in grooves formed between the adjacent wings. Furthermore, the more the number of the wings is, the smaller the size of each wing is, which can prevent the wings from swaying widely when the balloon is inflating. Moreover, the above configuration is suitable for industrial production because it does not need a process for wrapping the wings around the shaft when being manufactured.

Furthermore, according to a first to a seventh methods for manufacturing a balloon catheter, a balloon catheter having a region (first region) that retains medicine and a region (second region) that retains less medicine than the first region or that retains no medicine can be easily manufactured.

BRIEF DESCRIPTION OF THE DRAWINGS

FIG. 1 is a plan view showing a first and a second balloon catheters.

FIG. 2A is a sectional view of the balloon catheters taken along the line A-A in FIG. 1, and FIG. 2B is a sectional view of the balloon catheters taken along the line B-B in FIG. 1.

FIG. 3 is a perspective view showing a distal side of the first balloon catheter in a deflated state.

FIG. 4 is a front view of the first balloon catheter in a deflated state.

FIG. 5 is a front view of the balloon catheter, shown in FIG. 4, in an inflated state.

FIG. 6 is a front view of another first balloon catheter in a deflated state.

FIG. 7 is a front view of the balloon catheter shown in FIG. 6 in an inflated state.

FIG. 8 is a front view of still another first balloon catheter in a deflated state.

FIG. 9 is a front view of the balloon catheter shown in FIG. 8 in a folded state.

FIG. 10 is a front view of the balloon catheter shown in FIG. 8 in an inflated state.

FIG. 11 is a plan view of a balloon catheter for showing an example of disposition of a first region and a second region.

FIG. 12 is a plan view of a balloon catheter for showing another example of disposition of the first region and the second region.

FIG. 13 is a plan view of a balloon catheter for showing still another example of disposition of the first region and the second region.

FIG. 14 is a front view of a second balloon catheter in a deflated state.

FIG. 15 is a front view of another second balloon catheter in a deflated state.

FIG. 16 is a front view of still another second balloon catheter in a deflated state.

DETAILED DESCRIPTION OF THE EMBODIMENTS

Hereinafter, one or more embodiments of the present invention will be described in more detail by way of the following embodiments, however, the present invention is not limited to the following embodiments. It is obvious that one or more embodiments of the present invention can be carried out by making modifications, as appropriate, in accordance with the gist described above and below, and such modifications are also included in the technical scope of the present invention. Note that, in each drawing, hatching, reference signs for components, and the like may be omitted for convenience of description, and in such a case, the specification and other drawings are to be referred to. Further, the dimensions of the various components in the drawings are provided for the purpose of facilitating the understanding of the feature of the present invention, and the dimensions may differ from the actual dimensions in some cases.

(1) Common Structure of First and Second Balloon Catheters

Firstly, an overall configuration of a balloon catheter will be described with reference to FIGS. 1 and 2. FIG. 1 is a plan view of a first and a second balloon catheters, FIG. 2A is a sectional view of the balloon catheters taken along the line A-A in FIG. 1, and FIG. 2B is a sectional view of the balloon catheters taken along the line B-B in FIG. 1. FIG. 1 shows a configuration example of an over-the-wire balloon catheter in which a wire is inserted from a distal side to a proximal side of a shaft. The balloon catheter 1 has a shaft 2 and a balloon 10 disposed outside the shaft 2. The balloon catheter 1 has a proximal side and a distal side. The balloon 10 is provided on the distal side of the shaft and a hub 5 is provided on the proximal side of the shaft. In one or more embodiments of the present invention, the proximal side of the balloon catheter 1 is defined as a direction proximal to user (operator)'s hand with respect to the direction in which the balloon catheter 1 (particularly the shaft 2) extends, and the distal side is defined as a direction opposite to the proximal side (that is, a direction toward a target to be treated). A direction from the proximal side to the distal side of the balloon is referred to as an axial direction.

The balloon catheter 1 is configured such that a pressure fluid is supplied from the hub 5 to the inside of the balloon 10 through the shaft 2, and when the pressure fluid is supplied to the inside of the balloon 10, the balloon 10 can be inflated. Conversely, the balloon 10 can be deflated by removing the pressure fluid from the inside of the balloon 10.

Generally, the shaft 2 is internally provided with a pressure fluid flow path and a wire insertion path for a wire that guides the movement of the shaft. For example, the shaft 2 is composed of an inner tube 3 and an outer tube 4, wherein the inner tube 3 serves as the wire insertion path, and a space between the inner tube 3 and the outer tube 4 serves as the pressure fluid flow path. In this case, on the distal side of the shaft 2, the inner tube 3 extends from the distal end of the outer tube 4 and penetrates the balloon 10 in the axial direction. Thus, the distal side of the balloon 10 is connected to the inner tube 3, and the proximal side of the balloon 10 is connected to the outer tube 4.

The hub 5 has a fluid inlet portion 6 in communication with the pressure fluid flow path, and a manipulating portion 7 in communication with the wire insertion path. The manipulating portion 7, through which the wire is inserted, can also serve as an inlet for medicine or the like and as a suction port for fluid or the like in a living body cavity.

The balloon, the shaft (the inner tube and the outer tube), and the hub can be joined by using conventionally known joining methods such as a method using an adhesive or heat welding. Although not shown, a radiopaque marker may be disposed in the portion of the shaft where the balloon is located such that the position of the balloon can be checked by radioscopy.

One or more embodiments of the present invention are also applicable to a rapid exchange balloon catheter in which a wire is inserted from the distal side to a position at the middle between the distal side and the proximal side of the shaft. In this case, the wire insertion path may be provided in a part of the shaft including the distal side of the shaft, and the hub may not be provided with the manipulating portion.

The balloon can be manufactured by molding a resin. For example, the balloon can be produced by the following steps: extruding resin by extrusion molding to form a resin tube; setting the resin tube in a mold; and biaxially stretched blow molding the resin tube. The balloon can be formed into any shape according to the shape of the mold. The balloon can also be manufactured by a known molding method, such as dip molding, injection molding, or compression molding, besides biaxial stretch blow molding.

In many cases, a typical shape of the balloon is as shown in FIG. 2, in which a proximal taper portion 11 and a distal taper portion 12 are conical, and a straight tube portion 13 between the proximal taper portion 11 and the distal taper portion 12 is cylindrical, however, it is not limited thereto. For example, the straight tube portion 13 may be somewhat inclined according to, for example, the shape of a lesion as long as the angle of the inclination is smaller than the inclination angles of the proximal taper portion 11 and the distal taper portion 12.

The balloon may be a so-called non-compliant type, in which the balloon diameter hardly increases with an increase in an inflation pressure over a predetermined pressure, or may be a so-called semi-compliant type, in which the balloon diameter varies according to an inflation pressure. The type of the balloon can be selected, as appropriate, according to, for example, a site to which the balloon catheter is to be applied. In cases where the balloon catheter is used to dilate, for example, a narrowed portion sclerosed by calcification or the like, the non-compliant type may be preferably used.

Examples of the resin constituting the balloon include polyamide-based resin, polyester-based resin, polyurethane-based resin, polyolefin-based resin, vinyl chloride-based resin, silicone-based resin, and natural rubber. These may be used alone, or two or more of them may be used in combination. Among them, polyamide-based resin, polyester-based resin, and polyurethane-based resin may be preferably used. An elastomer resin may be preferably used for these resins from the viewpoint of flexibility and reduction in thickness of the balloon. Among polyamide-based resins, nylon 11 and nylon 12, for example, can be used as materials suitable for the balloon, and nylon 12 is suitably used because it can be relatively easily molded when being blow-molded. From the viewpoint of flexibility and reduction in thickness of the balloon, polyamide elastomer, such as polyether ester amide elastomer and polyamide ether elastomer, may be preferably used. Among them, polyether ester amide elastomer may be preferably used because it has high yield strength to provide dimensionally stable balloon. Furthermore, a reinforcing material may be provided on the balloon in order to enhance its performance in dilating the narrowed lesion sclerosed by calcification or the like and to enhance the dimensional stability against inflation pressure. A fiber material can be used as the reinforcing material, for example. Specifically, polyarylate fiber, aramid fiber, ultra-high molecular weight polyethylene fiber, PBO fiber, carbon fiber, and the like are suitably used. These fiber materials may be monofilament or multifilament.

The dimension of the balloon may be appropriately determined according to, for example, the size of a treated area.

For example, in cases where the treated area is a blood vessel, the balloon may preferably have an axial length of 5 mm to 300 mm and an outer diameter of 1 mm to 12 mm, and in cases where the treated area is a digestive tract such as a duodenal papilla, the balloon may preferably have an axial length of 10 mm to 100 mm and an outer diameter of 3 mm to 30 mm.

The medicine to be retained on the balloon is not particularly limited, as long as it is a pharmacologically active substance, and examples of the medicine include pharmaceutically acceptable drugs such as genetic therapeutic agents, non-genetic therapeutic agents, small molecules, and cells. Particularly, in cases where the balloon catheter is used to prevent an occurrence of restenosis in a blood vessel after treatment with angioplasty, anti-restenosis agents, such as an antiproliferative agent or an immunosuppressive agent can be preferably used. Specifically, agents such as paclitaxel, sirolimus (rapamycin), everolimus, or zotarolimus can be used. One kind or two or more kind thereof can be used.

The medicine may be attached on the outer surface of the balloon, may be impregnated into the balloon, or may be retained on the balloon in the form of microcapsules or the like. The medicine may also include an auxiliary agent for improving dispersibility, solubility, transferability to blood vessel walls, and storage stability of the medicine, together with pharmacologically active substances. Examples of usable auxiliary agents include stabilizers, bases, binders, excipients, disintegrants, moisture-proofing agents, antiseptics, solubilizers, and auxiliary solubilizers. Specific examples thereof include saccharides, such as lactose, white sugar, dextrin, xylitol, erythritol, mannitol, carboxymethyl cellulose, oxidized cellulose, hydroxy cellulose, or hydroxymethyl cellulose; benzoic acid salts, ethylenediamine, potassium iodide, urea, polysorbate, dibutylhydroxytoluene, sodium metabisulfite, ascorbic acid, tocopherol, benzoic acid, peroxybenzoic acid esters, benzalkonium chloride, gum arabic, alginate, and glycerin.

The medicine may be retained on the balloon in a state of being protected by a coating layer to prevent the medicine from eluting into blood or falling during being delivered. The coating layer can be formed from water-soluble polymers, hydrophobic polymers, saccharides, lipids, surfactants, or the like.

In addition, the auxiliary agent or the coating layer has advantages: the medicine can be placed on the balloon 10 in more amounts and in high density; and transferability of the placed medicine to a blood vessel wall can be improved. When the auxiliary agent or the coating layer is provided in an intended portion (for example, a first region) on the balloon 10, elution or fall of the placed medicine during being delivered to the lesion site can be prevented, and more medicine can be delivered to the target lesion. Since some medicine exert a therapeutic effect in a dose-dependent manner, placement of more medicine on the balloon 10 can contribute to improving the therapeutic effect.

In order to make it easier for the medicine retained on the balloon to transfer to inner walls of the blood vessels and the like by inflating the balloon for a long time, a perfusion type balloon catheter may be employed that has a perfusion lumen allowing blood and the like to move between the proximal side and the distal side of the balloon through the balloon. Although not shown, the balloon catheter may have one or more shafts and one or more balloons.

(2) First Balloon Catheter

Next, a first balloon catheter according to one or more embodiments of the present invention will be described in detail. A balloon of the first balloon catheter has fold lines. For example, the fold lines are formed by a method such as using a folding device for a balloon in a deflated state or deflating the balloon while portions that are to become fold lines are pressed (pleating). The fold lines function as a guide when the pleated balloon that has been inflated is spontaneously deflated by removing a pressure fluid to be re-folded (rewrapped).

FIG. 3 is a perspective view showing the distal side of the first balloon catheter in a deflated state. In FIG. 3, the distal taper portion and the proximal taper portion of the balloon are not illustrated. In one or more embodiments, the balloon has a plurality of wings, each having one main surface and the other main surface in the deflated state. Here, the one main surface of the balloon can also be restated as a first main surface and the other main surface as a second main surface. In FIG. 3, the balloon in a deflated state is provided with three wings 15 (15A, 15B, 15C). Accordingly, three convex fold lines 14 (14A) and three concave fold lines 14 (14B) are formed on the balloon. The outer diameter of the balloon can be reduced by wrapping the plurality of wings 15A, 15B, and 15C around the shaft 2, which make it easier for a balloon catheter to move while being delivered.

As shown in FIG. 3, the fold lines 14 may extend along the axial direction of the shaft 2. Although not shown, the fold lines 14 may helically extend around the axis of the shaft 2. Due to the fold lines 14 being formed as described above, the outer diameter of the balloon 10 when being folded can be decreased.

The number of the wings 15 is not particularly limited, however, 3 or more and 20 or less may be preferable, for example, and 7 or more and 12 or less may be more preferable. When the number of the wings 15 is 3 or more, the wings 15 can be satisfactorily wrapped around the shaft 2, which is advantageous for the balloon catheter to move and being operated at the narrowed portion and the lesion site. Furthermore, the more the number of the wings is, the smaller the size of each wing is, which prevents the wings 15 from swaying widely when the balloon 10 is inflating. The above configuration can prevent elution and loss of the medicine coated on the balloon caused by an impact of the swaying wings when the balloon 10 is inflating.

The balloon of the first balloon catheter according to one or more embodiments of the present invention has a first region that retains medicine on an outer surface and a second region that retains less medicine than the first region or that retains no medicine. Due to the second region provided in the first balloon catheter according to one or more embodiments of the present invention, it can prevent fall and elution of the medicine caused by spread of cracks generated in the first region retaining the medicine over the entire balloon.

Examples in which a second region 22 retains less medicine than a first region 21 will be described with reference to FIGS. 4 and 5. FIGS. 4 and 5 are front views of the balloon catheter as viewed from the distal side, wherein FIG. 4 shows the balloon in a deflated state, and FIG. 5 shows the balloon shown in FIG. 4 in an inflated state. The balloon 10 shown in FIGS. 4 and 5 has three wings 15A, 15B, and 15C in a deflated state. The second region 22 of the balloon 10 retains less medicine than the first region 21.

For example, a medicine layer is formed on the outer surface of the balloon 10, and it may be preferable that in the radial direction of the balloon 10, the medicine layer in the second region 22 is thinner than the medicine layer in the first region 21. The thickness of the medicine layer in the second region 22 may be preferably 70% or less, more preferably 50% or less, still more preferably 30% or less of the thickness of the medicine layer in the first region 21.

Forming the medicine layer in the second region 22 to be thinner than the medicine layer in the first region 21 makes cracks generated in the first region 21 less likely to spread over the entire balloon 10.

Examples in which medicine is not retained in the second region 22 will be described with reference to FIGS. 6 to 10. FIGS. 6 and 7 are front views of the balloon catheter as viewed from the distal side, wherein FIG. 6 shows the balloon in a deflated state, and FIG. 7 shows the balloon shown in FIG. 6 in an inflated state. The balloon 10 shown in FIGS. 6 and 7 has three wings 15A, 15B, and 15C in a deflated state. The second region 22 of the balloon 10 retains no medicine. Accordingly, cracks generated in the first region 21 remain within the first region 21, and thus, do not spread to adjacent first regions 21 and do not spread over the entire balloon 10.

As shown in FIGS. 8 to 10, the second region 22 retaining no medicine may be disposed only on one side surface of the wing 15. FIGS. 8 to 10 are front views of the balloon catheter as viewed from the distal side, wherein FIG. 8 shows the balloon in a deflated state, FIG. 9 shows the balloon shown in FIG. 8 in a folded state, and FIG. 10 shows the balloon shown in FIG. 8 in an inflated state. The balloon 10 shown in FIGS. 8 to 10 has three wings 15A, 15B, and 15C in a deflated state. As shown in FIG. 9, the wings 15A, 15B, and 15C are wrapped around the shaft 2. The first regions 21 (21A, 21B, 21C) are disposed on one main surfaces 16 (16A, 16B, 16C) of the plurality of wings 15A, 15B, and 15C, respectively. On the other hand, the second regions 22 (22A, 22B, 22C) are disposed on the other main surfaces 17 (17A, 17B, 17C) of the plurality of wings 15A, 15B, and 15C, respectively.

It may be preferable that the one main surfaces 16 of the wings 15 are disposed inwardly more than the other main surfaces 17 in the radial direction of the balloon 10 in a folded state. With this configuration, the first region 21 retaining medicine is less likely to be exposed to the outside, whereby elution of the medicine into blood and fall of the medicine can be prevented more effectively.

In FIG. 9, in a folded state in which the balloon 10 is wrapped around the shaft 2, one main surface (16A) of one wing 15 (15A, for example) is disposed outside the other main surface (17B) of another adjacent wing 15 (15B, for example) in the radial direction of the balloon 10. Accordingly, chance of peeling of the medicine retained between the wings diminishes that is due to impact or scrape during being delivered. As a consequence of disposing the first regions 21A, 21B, and 21C on the one main surfaces 16A. 16B, and 16C of the three wings 15A, 15B, and 15C, the medicine is retained only in the range of a half of the circumferential length of the inflated balloon 10 as shown in FIG. 10. Compared with the aspects in FIGS. 4 to 7, the balloon 10 retains less drug, however, the aspects shown in FIGS. 8 to 10 can effectively prevent elution and fall of the medicine in a folded state, thereby being capable of securing a necessary amount of the medicine when it reaches the lesion site or the narrowed portion. In addition, the lower amount of the medicine to be applied to the balloon 10 contributes to reduction in material cost.

Although not shown, the first region may be formed on the side of one main surfaces of the plurality of wings and an area that is covered by another wing on the side of the other main surface of one wing, when the wings are folded. A certain space is formed between the one wing and the another wing that covers a part on the side of the other main surface of the one wing, and thus, more drug can be retained in this area than in an area not covered by another wing.

Generally the balloon 10 is configured such that the straight tube portion 13 that defines the outermost diameter of the balloon 10 is actively brought into contact with a narrowed portion or a lesion site, and thus, an amount of the medicine retained on the straight tube portion 13 is larger than the amount of the medicine retained on the proximal taper portion 11 and the distal taper portion 12. Therefore, the medicine retained on the straight tube portion 13 may often elute or fall unintentionally. In view of this, it may be preferable that the first region 21 and the second region 22 are provided at least in the straight tube portion 13 in the axial direction of the balloon 10.

The first region 21 may be preferably divided into at least two or more segments. In addition, it may be preferable that the first region 21 is divided into at least two or more segments by the second region 22. Furthermore, it may be preferable that the second region 22 is disposed between one segment and another segment of the first region 21. Cracks generated in the first region 21 are likely to remain within each segment. The number of segments may be, for example, 4 or more, 6 or more, 8 or more, 9 or more, 10 or more, 12 or more, 15 or more, 18 or more, 20 or more, or 21 or more. The number of segments may also be allowed to be 50 or less or 40 or less.

FIGS. 11 to 13 are plan views showing examples of disposition of the first region 21 and the second region 22. As shown in FIGS. 4 to 11, the second region 22 (22A, for example) may be preferably disposed between one segment (21A, for example) and another segment (21B, for example) of the first region 21 in the circumferential direction of the balloon. With this configuration, cracks generated in the first region 21 are less likely to spread in the circumferential direction. Circumferential lengths of each segment of the first region 21 may be the same or different from one another.

Distances between one segment and another adjacent segment of the first region 21 in the circumferential direction may be the same or different from one another.

As shown in FIGS. 4 to 11, it may be preferable that the first region 21 and the second region 22 are alternated in the circumferential direction of the balloon 10. This configuration can more effectively prevent cracks generated in the first region 21 from spreading in the circumferential direction.

In FIG. 11, two second regions 22A and 22B are disposed along the axial direction, and therefore, the first region 21 is divided into three segments 21A, 21B, and 21C. Thus, the second region 22 may preferably extend along the axial direction of the shaft 2. This configuration can prevent cracks generated in the first region 21 from spreading in the circumferential direction. In one or more embodiments, the second region 22 may preferably extend from the proximal end to the distal end of the straight tube portion 13, and may preferably extend from the proximal end of the proximal taper portion 11 to the distal end of the distal taper portion 12.

It may be preferable that the amount of the medicine retained at an edge part of the first region 21 of the balloon 10 gradually decreases toward the second region 22. By the gradual decrease of the amount of the medicine retained at the edge part of the first region 21 from the first region 21 toward the second region 22, cracks is less likely to be generated in the area where the amount of the medicine is gradually varied. For example, in cases where a medicine layer is formed on the outer surface of the balloon 10, it may be preferable that the thickness of the medicine layer at the edge part of the first region 21 gradually decreases toward the second region 22. Due to the medicine layer being formed as described above, cracks are less likely to be generated near the boundary between the first region 21 and the second region 22. Here, the edge part means a portion including the edge of the first region 21.

From the viewpoint of increasing the amount of the medicine to be retained, it may be preferable that the area of the first region 21 is larger than the area of the second region 22, and it may be more preferable that the sum of the areas of all first regions 21 is larger than the sum of the areas of all second regions 22. For the same reason, in the straight tube portion, the sum of the areas of all first regions 21 may be preferably twice or more, more preferably five times or more, still more preferably ten times or more the sum of the areas of all second regions 22.

In FIG. 12, three second regions 22A, 22B, and 22C are disposed in the circumferential direction, and therefore, the first region 21 is divided into four segments 21A, 21B, 21C, and 21D. Thus, the second region 22 may extend in the circumferential direction. This configuration can prevent cracks generated in the first region 21 from spreading in the axial direction. In one or more embodiments, the second region 22 extends along the entire circumference.

As shown in FIG. 13, the second region 22 may extend along the axial direction and the circumferential direction of the shaft 2. The first region 21 may be accordingly divided into two or more segments to have a mesh shape. This configuration can increase the number of segments of the first region 21. Lower amount of the medicine retained in the second region than the amount of the medicine retained in the first region can prevent cracks generated in the first region 21 from spreading in the circumferential direction and the axial direction.

In cases where the medicine is not retained in the second region, the cracks generated in the first region 21 remain within the first region 21 itself, so that the cracks do not spread to the other first regions at all.

The first region 21 disposed at the fold line of the balloon may cause cracks in the first region 21 due to the difference in hardness between the balloon 10 and the medicine, which may result in peeling or elution of the medicine. In view of this, the second region 22 may be preferably disposed on the fold line 14 as shown in FIGS. 4 to 7. In addition, it may be preferable that the first region 21 is not disposed on the fold line 14. This configuration can prevent cracks which starting point is the fold line 14 from spreading to the first region 21.

As shown in FIGS. 4, 6, and 8, when the balloon 10 in a deflated state is viewed from the distal side, convex fold lines 14A and concave fold lines 14B are alternated in the circumferential direction. When the balloon is folded, the convex fold lines 14A are located outwardly more than the concave fold lines 14B in the radial direction. Therefore, the second region 22 may be preferably disposed at least at the convex fold lines 14A.

It may be preferable that the second region 22 is disposed at both the convex fold lines 14A and the concave fold lines 14B in order to prevent cracks which starting point is the fold line 14 from spreading to the first regions 21. Alternatively, the first region 21 may be disposed at the concave fold lines 14B, because the concave fold lines 14B is hardly exposed to the outside when the wings 15 are wrapped.

Although not shown, the balloon 10 may have, as still another aspect, a second region 22 retaining no medicine and a second region 22 retaining medicine in an amount less than the amount of the medicine retained in the first region. Specifically the second region 22 retaining no medicine may be disposed at one fold line and the second region retaining the medicine in an amount less than the amount of the medicine retained in the first region may be disposed at another fold line. For example, the balloon 10 may be configured such that the second region 22 retaining no medicine is disposed at the convex fold lines 14A and the second region retaining the medicine in an amount less than the amount of the medicine retained in the first region is disposed at the concave fold lines 14B. With this configuration, cracks which starting point is the convex fold lines, that is likely to be exposed to the outside and is likely to cause unintentional elution or fall of the medicine, do not spread to the first region 21. This configuration can also prevent cracks which starting point is the concave fold lines from spreading to the first region 21 and can increase the amount of the medicine to be retained, as compared to the case where no medicine is retained in the second region.

A thinner medicine layer than the medicine layer in the first region 21 may be formed at the convex fold lines. The thickness of the medicine layer at the convex fold lines may be preferably 50% or less of the thickness of the medicine layer in the first region 21. This configuration can effectively prevent the medicine from eluting and falling in a folded state, and also prevent cracks generated in the first region from spreading in the circumferential direction.

(3) Second Balloon Catheter

A second balloon catheter according to one or more embodiments of the present invention has a balloon that retains medicine on its outer surface. The balloon of the second balloon catheter includes a balloon that does not need to be folded with wings being wrapped around a shaft.

The balloon has 7 or more and 20 or less wings in a deflated state. Setting the number of wings of the balloon in a deflated state in the above range makes it easier for the medicine to be retained in grooves formed between the adjacent wings. In addition, the more the number of the wings is, the smaller the size of one wing is, which can prevent the wings from widely swaying when the balloon is inflating. Moreover the above configuration is suitable for industrial production because it does not need a process for wrapping the wings around the shaft when being manufactured.

The number of wings of the balloon may be more preferably 8 or more, and still more preferably 10 or more. The more the number of wings of the balloon is, the more the number of grooves formed between adjacent wings, which makes the cracks generated in the medicine likely to remain within the respective grooves. From a standpoint of easiness in production, the number of wings may be more preferably 18 or less, and still more preferably 12 or less.

The medicine may be preferably retained inside of the maximum length of the wings in the radial direction of the balloon. The medicine is divided into a plurality of segments by the wings, and therefore, even if cracks are generated in the medicine retained in one groove, such cracks are less likely to spread to the medicine retained in another groove adjacent to the one groove.

FIGS. 14 to 16 are front views of the second balloon catheter as viewed from the distal side. The balloon 10 shown in FIG. 14 has 18 wings 15 in a deflated state. Grooves 18 are formed between the adjacent wings 15 and 15, and medicine 20 is retained in the grooves 18.

Although not shown, the balloon may be configured to have first wings and second wings longer than the first wings in the radial direction in a deflated state, the first wings and the second wings being alternated in the circumferential direction of the balloon. This prevents the adjacent wings from contacting each other when the balloon is inflating.

As shown in FIG. 15, one wing 15 and another wing 15 may be separated from each other in the circumferential direction of the deflated balloon 10. That is, the adjacent wings 15 and 15 may not be in contact with each other in the circumferential direction of the deflated balloon 10. This configuration can prevent the adjacent wings 15 and 15 from contacting each other when the balloon 10 is inflating. When the position of the wings 15 at the outermost diameter of the inflated balloon 10 is defined as 100% and the position of the axis of the shaft 2 is defined as 0%, the position where the adjacent wings 15 and 15 are closest to each other in the radial direction may be preferably located inside the position of 90%, more preferably inside the position of 80%. With this configuration, the grooves 18 between the adjacent wings 15 and 15 becomes deeper, which makes it easier to retain the medicine. On the other hand, in order to prevent the wings 15 and 15 from contacting each other when the balloon 10 is inflating, the position where the adjacent wings 15 and 15 are closest to each other in the radial direction may be located outside the position of 30%, more preferably outside the position of 40%, based on the definition.

As shown in FIG. 16, the wings 15 may have bent portions 19 protruding outward in the radial direction. The radially inner side of the bent portions 19 functions as a pocket for retaining the medicine. Note that, in FIG. 16, the bent portions 19 are provided to all of the wings 15, however, the bent portions 19 may be provided only to some of the all wings. For example, the wing 15 provided with the bent portion 19 and the wing 15 not provided with the bent portion 19 may be alternated in the circumferential direction.

In order to prevent the medicine 20 from falling, a coating layer 25 may be provided on the outside of the balloon as shown in FIGS. 14 to 16. The coating layer 25 can be formed in the same manner as in a method for applying medicine described later. The coating layer may be provided in the first region and/or the second region. Alternatively, the coating layer may be provided only in the first region and not in the second region.

(4) Manufacturing Method

A method for manufacturing the balloon catheter according to one or more embodiments of the present invention capable of preventing medicine from eluting into blood and falling during being delivered will now be described.

(A) First Manufacturing Method (A-1) Preparing Balloon

First, a balloon having a plurality of wings in a deflated state is prepared. Here, the balloon to be prepared is of the type that is finally wrapped around a shaft to be folded. The balloon can be manufactured by the following method (a) or (b), for example.

(a) First, a balloon manufacturing tube (parison) having a predetermined inside diameter and a predetermined outside diameter is produced from a resin by extrusion molding. In this case, a mold of an extruder having a predetermined shape may be used to manufacture a tube having a shape of a prototype of the wings. It may be preferable that portions that are to be molded as the proximal taper portion and the distal taper portion are stretched in the axial direction while they are locally heated. With this process, the tapered portions after the molding process can be sufficiently reduced in thickness. The portion that has been reduced in thickness by stretching is cut while leaving a predetermined length, whereby a preformed parison is formed.

Next, the parison preformed to have a predetermined length is transferred to a cavity in a blow molding mold, and the molding mold is closed. Then, compressed air is blown to the inside of the mold to inflate the parison, so that the parison is molded into the cavity shape. Thus, the straight tube portion and the tapered portions of the balloon are formed. The blow molding may be performed under heating conditions or may be performed several times. Further, radial stretching and axial stretching may be simultaneously performed, or after either the radial stretching or axial stretching is performed, and then, the other may be performed. A balloon having a shape of a prototype of wings can also be manufactured by using a blow molding mold having a predetermined shape. In order to fix the shapes and dimensions of fold lines and wings on the balloon to improve foldability during rewrapping or to increase strength, the balloon may be preferably heat fixed when the compressed air is removed from the balloon after the blow molding. Specifically, it may be preferable that the compressed air is removed from the inside of the balloon in either a state where the portion that is to be formed as a fold line is pressed or a state where a mold having a predetermined shape is contacted with the balloon.

(b) A balloon manufacturing tube (parison) is prepared by extrusion molding in the same manner as in the method (a). A core material having a predetermined shape is placed in the lumen of the parison. The parison having the core material placed therein is placed in the lumen of a heat shrinkable tube, and hot air is applied to the heat shrinkable tube. The parison shrinks, and thus, the preformed parison can be manufactured that has a circular outside shape and an inside shape equal to the outer shape of the core material. Thereafter, steps same as the steps in the method (a) are performed, whereby the balloon can be manufactured by blow molding using the preformed parison.

(A-2) Inflating Balloon and Forming Mask

A pressure fluid is supplied to the inside of the balloon to inflate the balloon. A mask is formed in a predetermined region (for example, a straight tube portion of the balloon) of the inflated balloon. The region where the mask is formed retains no medicine, and therefore, the predetermined region of the balloon corresponds to the second region of the first balloon catheter. In addition, the first region can be formed by performing a mask removing step that will be described later. The predetermined region serving as the second region can be formed to have any shape. A medical masking tape, a metal mold, or a jig can be used for the mask, for example. It may be preferable that, to form a balloon having a second region that retains less medicine than the first region, the mask is formed on the balloon on which the medicine has been retained in advance, and more medicine is attached to the balloon to be retained in step (A-3) described later. The mask may have a predetermined structure designed such that the medicine coating applied on the balloon is less likely to have a starting point of peeling (crack). The mask may have a structure capable of fixing the mask to the balloon, and examples include a mask having a structure for gripping the proximal taper portion 11 and the distal taper portion 12 of the balloon, a mask having a structure for gripping the shaft 2, a mask having a structure for gripping the second region, and a mask having a structure for gripping the balloon so as to nip the wings of the balloon. Further, examples of the mask include a mask having a structure in which only the first region or the second region is exposed when the mask is fixed to the balloon, and a mask having a structure provided with a window such that a region corresponding to the first region or the second region can be opened or closed.

(A-3) Attaching Medicine to Balloon to be Retained

Medicine is attached to the balloon on which the mask has been formed, and the medicine is retained on the balloon. Examples of a method for attaching the medicine include a method for applying medicine in a solid or liquid state or medicine in the form of a solution containing a solvent to the outer surface of the balloon. Especially, from the viewpoint of easiness of coating, the method for applying medicine in the form of a solution containing a solvent may be preferable. It may be preferable that, when the balloon is divided into two, an inner portion and an outer portion, in the radial direction of the balloon with the wings of the balloon being folded, the amount of the medicine retained in the radially inner portion is larger than the amount of the medicine retained in the radially outer portion. It may be preferable that the amount of the medicine applied to the one main surface facing radially inward is larger than the amount of the medicine on the other main surface facing radially outward.

Examples of the application method include brush coating, roll coater coating, dip coating, spray coating, comma coating, knife coating, die coating, dice coating, lip coating, and curtain coating. Especially, from the viewpoint of easiness of coating, dip coating and spray coating may be preferable. The medicine may be applied only one time or two or more times.

The type of solvent usable for applying the medicine is not particularly limited as long as the solvent can dissolve or disperse the medicine. From the viewpoints of availability and bioavailability (safety), examples of the solvent include ethanol, methanol, acetone, ethyl acetate, acetonitrile, N,N-dimethylacetamide, propanol, chloroform, and benzyl alcohol, and particularly, ethanol and acetone may be preferable.

(A-4) Removing Mask

The mask formed on the balloon is removed. For example, the medical masking tape attached to the balloon is peeled, or the mold or jig is removed. According to the first manufacturing method, the balloon catheter having a region (first region) that retains medicine and a region (second region) that retains less medicine than the first region or that retains no medicine can be easily manufactured.

(A-5) Connecting Components

A shaft, a hub, and the balloon are connected. In one or more embodiments, the shaft can be manufactured from a material analogous to materials preferable for the balloon, by extrusion molding, for example. The hub can be manufactured from a material, for example, a synthetic resin such as ABS and polycarbonate by, for example, injection molding. The shaft, the hub and the balloon may be connected after step (A-4) or after step (A-1).

(A-6) Folding Balloon

The pressure fluid in the balloon from which the mask has been removed is removed to deflate the balloon. The wings of the deflated balloon are folded manually or with a folding device.

(A-7) Forming Coating Layer

Although not essential, medicine may be retained on the balloon while being protected by a coating layer to prevent the medicine from eluting into blood or falling during being delivered. Therefore, the first manufacturing method may include a step for forming the coating layer on the deflated balloon with the wings being folded. The coating layer can be formed from water-soluble polymers, hydrophobic polymers, saccharides, lipids, surfactants, and the like.

(B) Second Manufacturing Method (B-1) Preparing Balloon

In the same manner as in step (A-1) of the first manufacturing method, a balloon having a plurality of wings in a deflated state is prepared.

(B-2) Inflating Balloon and Applying Medicine

The balloon is inflated, and medicine is applied to a predetermined region of the balloon. The predetermined region corresponds to the first region of the first balloon catheter. According to the second manufacturing method, the balloon catheter having a region (first region) that retains medicine and a region (second region) that retains less medicine than the first region or that retains no medicine can be easily manufactured. The medicine can be applied in the same manner as in step (A-3) of the first manufacturing method.

(B-3) Folding Balloon

In the same manner as in step (A-6) of the first manufacturing method, the balloon to which the medicine is applied is deflated and the wings of the balloon are folded.

(B-4) Others

The shaft, the hub, and the balloon can be connected by referring to step (A-5) of the first manufacturing method. The second manufacturing method may include a step for forming a coating layer on the folded balloon as in step (A-7).

(C) Third Manufacturing Method (C-1) Preparing Balloon

In the same manner as in step (A-1) of the first manufacturing method, a balloon having a plurality of wings in a deflated state is prepared.

(C-2) Inflating Balloon and Having Balloon Retaining Medicine

The balloon is inflated, and medicine is attached to the balloon to be retained in the same manner as in step (A-3) of the first manufacturing method. It may be preferable that the medicine is retained on at least the straight tube portion of the balloon, and it may be preferable that the medicine is retained on the entire balloon.

(C-3) Removing Medicine

The medicine in the predetermined region is removed. Examples of a method for removing the medicine include scraping the medicine with a file, a squeegee or the like, and removing the medicine with a removing agent. According to the third manufacturing method having the step for removing the medicine, the balloon catheter having a region (first region) that retains medicine and a region (second region) that retains less medicine than the first region or that retains no medicine can be easily manufactured.

(C-4) Folding Balloon

In the same manner as in step (A-6) of the first manufacturing method, the balloon from which the drug has been removed is deflated and the wings of the balloon are folded.

(C-5) Others

The shaft, the hub, and the balloon can be connected by referring to step (A-5) of the first manufacturing method. The third manufacturing method may include a step for forming a coating layer on the folded balloon as in step (A-7).

(D) Fourth Manufacturing Method (D-1) Preparing Balloon

In the same manner as in step (A-1) of the first manufacturing method, a balloon having a plurality of wings in a deflated state is prepared.

(D-2) Folding Balloon

In the same manner as in step (A-6) of the first manufacturing method, the wings of the deflated balloon are folded.

(D-3) Having Balloon Retaining Medicine

In the same manner as in step (A-3) of the first manufacturing method, medicine is attached to the folded balloon to be retained. By the fourth manufacturing method, the medicine is attached on the folded balloon, whereby a region retaining no medicine when the balloon is inflated can be formed. Therefore, the step of inflating the balloon for attaching medicine to the balloon can be eliminated.

(D-4) Others

The shaft, the hub, and the balloon can be connected by referring to step (A-5) of the first manufacturing method. The fourth manufacturing method may include a step for forming a coating layer on the folded balloon as in step (A-7). It may be preferable that the coating layer is formed after step (D-3) in which the medicine is attached to the folded balloon to be retained.

(E) Fifth Manufacturing Method (E-1) Preparing Balloon

In the same manner as in step (A-1) of the first manufacturing method, a balloon having a plurality of wings in a deflated state is prepared.

(E-2) Forming Mask

A mask is formed in a predetermined region of the balloon having wings. The mask is formed in the same manner as in step (A-2) of the first manufacturing method, except that the mask is formed on the balloon in a deflated state without inflating the balloon.

(E-3) Having Balloon Retaining Medicine

In the same manner as in step (A-3) of the first manufacturing method, medicine is attached to the deflated balloon on which the mask has been formed, and the medicine is retained on the balloon.

(E-4) Removing Mask

In the same manner as in step (A-4) of the first manufacturing method, the mask is removed from the deflated balloon.

(E-5) Folding Balloon

The wings of the deflated balloon are folded in the same manner as in step (A-6) of the first manufacturing method, except that the step for deflating the balloon is unnecessary. Therefore, according to the fifth manufacturing method, the balloon catheter having the first region and the second region can be easily manufactured while skipping the step of inflating the balloon for attaching medicine to the balloon.

(E-6) Others

The shaft, the hub, and the balloon can be connected by referring to step (A-5) of the first manufacturing method. The fifth manufacturing method may include a step for forming a coating layer on the folded balloon as in step (A-7).

(F) Sixth Manufacturing Method (F-1) Preparing Balloon

In the same manner as in step (B-1) of the second manufacturing method, a balloon catheter having a plurality of wings in a deflated state is prepared.

(F-2) Applying Medicine

Medicine is applied to a predetermined region of the balloon having wings in the same manner as in step (B-2) of the second manufacturing method, except that the medicine is applied to the balloon in a deflated state without inflating the balloon.

(F-3) Folding Balloon

The wings of the deflated balloon are folded in the same manner as in step (B-3) of the second manufacturing method, except that the step for deflating the balloon is unnecessary. Therefore, according to the sixth manufacturing method, the balloon catheter having the first region and the second region can be easily manufactured while skipping the step of inflating the balloon for attaching medicine to the balloon.

(F-4) Others

The shaft, the hub, and the balloon can be connected by referring to step (A-5) of the first manufacturing method.

The sixth manufacturing method may include a step for forming a coating layer on the folded balloon as in step (A-7).

(G) Seventh Manufacturing Method (G-1) Preparing Balloon

In the same manner as in step (C-1) of the third manufacturing method, a balloon having a plurality of wings in a deflated state is prepared.

(G-2) Attaching Medicine to Balloon to be Retained

Medicine is attached to a predetermined region in the same manner as in step (C-2) of the third manufacturing method, except that the medicine is attached on the balloon in a deflated state without inflating the balloon.

(G-3) Removing Medicine

In the same manner as in step (C-3) of the third manufacturing method, the medicine in the predetermined region is removed from the deflated balloon.

(G-4) Folding Balloon

The wings of the balloon from which the medicine has been removed are folded in the same manner as in step (C-4) of the third manufacturing method, except that the step for deflating the balloon is unnecessary. Therefore, according to the seventh manufacturing method, the balloon catheter having the first region and the second region can be easily manufactured while skipping the step of inflating the balloon for attaching the medicine to the balloon.

(G-5) Others

The shaft, the hub, and the balloon can be connected by referring to step (A-5) of the first manufacturing method. The seventh manufacturing method may include a step for forming a coating layer on the folded balloon as in step (A-7).

This application claims benefit of priority based on Japanese Patent Application No. 2016-132850 filed on Jul. 4, 2016. The entire contents of the specification of Japanese Patent Application No. 2016-132850 filed on Jul. 4, 2016 are incorporated herein by way of reference.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

DESCRIPTION OF REFERENCE SIGNS

1: Balloon catheter
2: Shaft
3: Inner tube
4: Outer tube
10: Balloon
11: Proximal taper portion
12: Distal taper portion
13: Straight tube portion
14: Fold line
14A: Convex fold line
14B: Concave fold line
15, 15A, 15B, 15C: Wing
16, 16A, 16B, 16C: One main surface (first surface)
17, 17A, 17B, 17C: Other main surface (second surface)
18: Groove
19: Bent portion
20: Medicine
21, 21A, 21B, 21C, 21D: First region
22, 22A, 22B, 22C: Second region
25: Coating layer

What is claimed is:

1. A balloon catheter comprising:
   a shaft; and
   a balloon having one or more fold lines,
   wherein the balloon is disposed outside the shaft,
   wherein the balloon comprises one or more first regions and one or more second regions,
   wherein the one or more first regions retain medicine on an outer surface of the balloon,
   wherein the one or more second regions retain some medicine, said some medicine being less medicine than the medicine retained on the one or more first regions,
   wherein the balloon comprises a plurality of wings each having first and second surfaces in a deflated state,
   wherein the one or more first regions are located on the first and second surfaces of each of the plurality of wings, and
   wherein the one or more first regions and the one or more second regions are alternately disposed in a circumferential direction of the balloon in an inflated state.

2. The balloon catheter according to claim 1, wherein the one or more first regions are divided into at least two segments.

3. The balloon catheter according to claim 1, wherein the one or more second regions are located at the one or more fold lines.

4. The balloon catheter according to claim 1,
   wherein the first surface of each of the plurality of wings is disposed more inwardly than the second surface in a radial direction of the balloon in a state in which the balloon is folded.

5. The balloon catheter according to claim 1, wherein the medicine is an antiproliferative agent or an immunosuppressive agent.

6. A balloon catheter comprising:
   a shaft; and
   a balloon having one or more fold lines,
   wherein the balloon is disposed outside the shaft,
   wherein the balloon comprises one or more first regions and one or more second regions,
   wherein the one or more first regions retain medicine on an outer surface of the balloon,
   wherein the one or more second regions retain less medicine than the one or more first regions or retain no medicine,
   wherein the balloon comprises a plurality of wings each having first and second surfaces in a deflated state, and
   wherein the one or more first regions are located on the first and second surfaces of each of the plurality of wings,
   wherein the one or more first regions and the one or more second regions are alternately disposed in a circumferential direction of the balloon in an inflated state,
   wherein the one or more fold lines of the balloon are one or more convex fold lines and one or more concave fold lines,
   wherein the one or more second regions are one or more second regions A that retain some medicine, said some medicine being less medicine than the medicine retained on the one or more first regions and one or more second regions B that retain no medicine,
   wherein the one or more second regions A, that retain less medicine than the one or more first regions, are located at the one or more concave fold lines, and
   wherein the one or more second regions B, that retain no medicine, are located at the one or more convex fold lines, such that cracks whose starting points are the one or more concave fold lines are prevented from spreading to the one or more first regions, wherein the cracks are generated from a difference in hardness between the balloon catheter and the medicine.

* * * * *